United States Patent [19]

Fischli et al.

[11] Patent Number: 4,927,958

[45] Date of Patent: May 22, 1990

[54] STYRYL KETONES

[75] Inventors: Albert Fischli, Riehen, Switzerland; Eva-Maria Gutknecht, Buggingen-Seefelden, Fed. Rep. of Germany; Daniel Obrecht, Basel, Switzerland

[73] Assignee: Hoffmann-La Roche Inc., Nutley, N.J.

[21] Appl. No.: 169,570

[22] Filed: Mar. 17, 1988

[30] Foreign Application Priority Data

Mar. 20, 1987 [CH] Switzerland ............ 1071/87

[51] Int. Cl.$^5$ ............................................. C07C 69/76
[52] U.S. Cl. .................................... 560/53; 562/426; 562/433; 562/452; 562/459; 562/463; 560/9; 560/19; 560/42; 560/51; 546/189; 548/530; 549/362; 564/161; 564/162; 564/163; 564/169; 568/308; 568/592; 514/538; 514/539; 514/545; 514/561; 514/570
[58] Field of Search ............... 560/53, 9, 19, 42, 51; 562/426, 433, 452, 459, 463; 546/189; 548/530; 549/362; 564/161, 162, 163, 169; 568/308, 592; 514/538, 539, 545, 561, 570

[56] References Cited

FOREIGN PATENT DOCUMENTS 3012584 10/1980 Fed. Rep. of Germany .

OTHER PUBLICATIONS

Wiley et al, CA 11728 (62), 1965.

Primary Examiner—Paul J. Killos
Attorney, Agent, or Firm—George M. Gould; Bernard S. Leon; A. Kate Huffman

[57] ABSTRACT

Styryl ketones of the formula

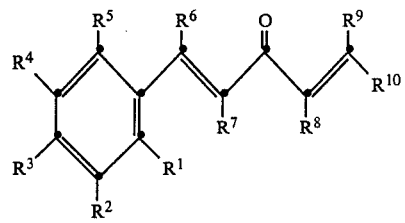

wherein
$R^8$ and $R^9$ are independently hydrogen or lower alkyl or together represent an additional carbon-carbon bond and
$R^{10}$ is a group of the formula $$-COOR^{11}, \quad -CONR^{12}R^{13}, \quad -C(R^{14})=O,$$
(a) (b) (c)

$$-C(R^{15})(OR^{16})_2, \quad -C(OR^{17})_3 \text{ or}$$
(d) (e)

$$-C(R^{18})(R^{19})OR^{20};$$
(f)

as well as corresponding compounds of the formula

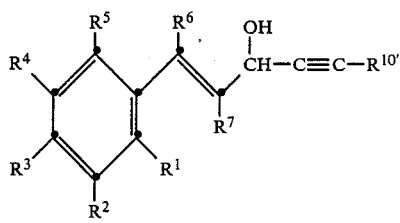

wherein $R^{10'}$ is a group of formula (a), (b), (d) or (e) or a group of the formula $$-C(R^{18})(R^{19})OR^{20'}; \quad (f')$$

have mucosa-protective and/or gastric acid secretion-inhibiting properties, such that they can be used for the control or prevention of illnesses of the gastrointestinal tract, especially against gastric ulcers or duodenal ulcers.

26 Claims, No Drawings

STYRYL KETONES

DESCRIPTION OF THE INVENTION

The present invention relates to styryl ketones. In particular, it comprises styryl ketones of the formula

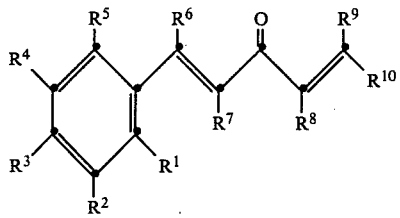

I wherein $R^1$, $R^2$, $R^3$, $R^4$ and $R^5$ are independently hydrogen, halogen, lower alkyl, lower alkoxy-lower alkyl, hydroxy, lower alkoxy, lower alkenyloxy, lower alkynyloxy, lower alkoxy-lower alkoxy, acyloxy, aryl-lower alkoxy, lower alkylthio, lower alkoxy-lower alkylthio, lower alkenylthio, lower alkynylthio, aryl-lower alkylthio, optionally substituted amino or trifluoromethyl, or two of these substituents which are adjacent jointly and together with the carbon atoms to which they are attached form a 5- to 7-membered ring, and wherein of the substituents $R^1$ to $R^5$ at least two are hydrogen and at least one is different from hydrogen; $R^6$ and $R^7$ are independently hydrogen or lower alkyl; $R^8$ and $R^9$ are independently hydrogen or lower alkyl or together represent an additional carbon-carbon bond; $R^{10}$ is a group of the formula

—COOR$^{11}$, —CONR$^{12}$R$^{13}$, —C(R$^{14}$)=O, (a)  (b)  (c)

—C(R$^{15}$)(OR$^{16}$)$_2$, —C(OR$^{17}$)$_3$ or (d)  (e)

—C(R$^{18}$)(R$^{19}$)OR$^{20}$;

(f)

$R^{11}$ is hydrogen, lower alkyl, lower alkenyl, lower alkoxy-lower alkyl, lower alkoxy-lower alkoxy-lower alkyl, aryl or aryl-lower alkyl; $R^{12}$ and $R^{13}$ are independently hydrogen or lower alkyl or jointly and together with the nitrogen atom represent a 5- to 7-membered saturated heterocyclic group; $R^{14}$ is lower alkyl, aryl or aryl-lower alkyl; $R^{15}$ is hydrogen, lower alkyl, aryl or aryl-lower alkyl; $R^{16}$ is lower alkyl or lower alkoxy-lower alkyl; $R^{17}$ is lower alkyl; $R^{18}$ and $R^{19}$ are independently hydrogen, lower alkyl, aryl or aryl-lower alkyl; and $R^{20}$ is hydrogen, lower alkyl, lower alkoxy-lower alkyl, lower alkenyl, lower alkynyl, acyl or aryl-lower alkyl;
in which the double bond(s) present in the molecule has (have) the E- and/or Z-configuration; as well as pharmaceutically acceptable salts of acidic compounds of formula I with bases and of basic compounds of formula I with acids.

These compounds are novel and they possess valuable pharmacodynamic properties, more specifically, mucosa-protective and/or gastric acid secretion-inhibiting properties. Thus, they can be used for the control or prevention of illnesses of the gastrointestinal tract, especially against gastric ulcers and/or duodenal ulcers.

Other facets of the present invention, in addition to these styryl ketones and salts, are pharmaceutical compositions containing these styryl ketones and salts, as well as the use of the styryl ketones and salts in the control or prevention of illnesses, especially in the control or prevention of gastric ulcers and/or duodenal ulcers.

The term "lower" denotes compounds or groups with a maximum of 7, preferably a maximum of 4, carbon atoms.

The term "alkyl" denotes straight-chain or branched saturated hydrocarbon groups such as methyl, ethyl, n-butyl and the like. The terms "alkoxy" and "alkylthio" denote alkyl groups in the sense of the previous definition attached via an oxygen atom and a sulphur atom, respectively, such as methoxy, methylthio, and the like. The terms "alkenyl" and "alkynyl" denote hydrocarbon groups which contain a carbon-carbon double or triple bond, e.g., groups such as dimethylallyl. The term "aryl" denotes an optionally substituted phenyl group such as 3,4,5-trimethoxyphenyl. The term "acyl" embraces lower alkanoyl groups such as acetyl or the like and aroyl groups such as 3,4,5-trimethoxybenzoyl and the like. The term "halogen" embraces the four forms: chlorine, fluorine, bromine and iodine. The term "optionally substituted amino" denotes an amino group which can be monosubstituted by lower alkyl or acyl or disubstituted by lower alkyl and acyl or by two lower alkyl groups.

The 5- to 7-membered ring which two adjacent substituents $R^1$, $R^2$, $R^3$, $R^4$, $R^5$ together with the carbon atoms to which they are attached can form, can be heterocyclic or carbocyclic. It can optionally contain one or more additional double bonds, in which case it can be aromatic or non-aromatic, and it can be substituted or unsubstituted. The 5- to 7-membered saturated heterocyclic group which $R^{12}$ and $R^{13}$ together with the nitrogen atom can form, can contain an additional hetero atom and it can be substituted or unsubstituted.

In formula I, by way of illustration, $R^1$ and $R^2$ can be hydrogen and $R^3$, $R^4$ and $R^5$ can be lower alkoxy; or $R^1$ and $R^5$ can be hydrogen and $R^2$, $R^3$ and $R^4$ can independently be lower alkoxy; or $R^1$, $R^2$ and $R^4$ can be hydrogen and $R^3$ and $R^5$ can be lower alkoxy; or $R^1$, $R^3$ and $R^4$ can be hydrogen and $R^2$ and $R^5$ can be lower alkoxy; or $R^1$, $R^2$ and $R^5$ can be hydrogen, $R^3$ can be hydroxy and $R^4$ can be lower alkoxy or $R^3$ and $R^4$ together can be lower alkylenedioxy; or $R^1$, $R^2$, $R^4$ and $R^5$ can be hydrogen and $R^3$ can be halogen, lower alkoxy, lower alkylthio or trifluoromethyl; or $R^1$, $R^2$, $R^3$ and $R^5$ can be hydrogen and $R^4$ can be lower alkoxy.

Furthermore, in formula I $R^{10}$ can be a group of formula (a), (d) or (f), $R^{11}$ can be hydrogen, lower alkyl or lower alkoxy-lower-alkoxy-lower-alkyl, $R^{15}$ can be hydrogen, $R^{16}$ can be lower alkyl, $R^{18}$ and $R^{19}$ can be hydrogen and $R^{20}$ can be hydrogen, lower alkoxy-lower alkyl or lower alkenyl.

Preferably, in formula I $R^1$, $R^2$, $R^4$ and $R^5$ are hydrogen and $R^3$ is fluorine or methoxy, or $R^1$, $R^2$, $R^3$ and $R^5$ are hydrogen and $R^4$ is methoxy; $R^6$ and $R^7$ are hydrogen; $R^8$ and $R^9$ are hydrogen or together represent an additional carbon-carbon bond; $R^{10}$ is a group of formula (a) or (f) in which $R^{11}$ preferably is hydrogen, methyl or methoxyethoxyethyl; and $R^{20}$ is hydrogen or 1-ethoxyethyl.

Especially preferred styryl ketones of formula I are the following:

(E,E)-6-(3-Methoxyphenyl)-4-oxo-2,5-hexadienoic acid;
(E,E)-6-(4-methoxyphenyl)-4-oxo-2,5-hexadienoic acid;
methyl (2Z,5E)-6-(4-methoxyphenyl)-4-oxo-2,5-hexadienoate and
(E)-6-(4-methoxyphenyl)-4-oxo-5-hexen-2-ynoic acid.

Further preferred styryl ketones of formula I are:

(E,E)-6-(4-Fluorophenyl)-4-oxo-2,5-hexadienoic acid;
(2Z,5E)-6-(4-methoxyphenyl)-4-oxo-2,5-hexadienoic acid;
2-(2-methoxyethoxy)ethyl (E,E)-6-(3-methoxyphenyl)-4-oxo-2,5-hexadienoate and
2-(2-methoxyethoxy)ethyl (E)-6-(4-methoxyphenyl)-4-oxo-5-hexen-2-ynoate.

The styryl ketones of formula I and their salts can be prepared by the following methods:

(a) oxidizing a compound of the formula

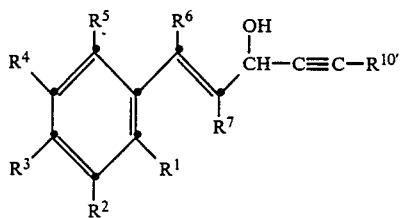

wherein $R^1$, $R^2$, $R^3$, $R^4$, $R^5$, $R^6$ and $R^7$ are as defined above and $R^{10'}$ is a group of formula (a), (b), (d) or (e) or a group of the formula $$-C(R^{18})(R^{19})OR^{20'} \qquad (f')$$

in which $R^{18}$ and $R^{19}$ are as defined above and $R^{20'}$ has the same meaning defined above for $R^{20}$ but is not hydrogen when $R^{18}$ and/or $R^{19}$ is hydrogen;

or (b) treating a compound of formula II, above, in which $R^{10'}$ is a group of formula (a), but in which $R^{11}$ is not hydrogen, with a base; or (c) reacting a compound of the formula

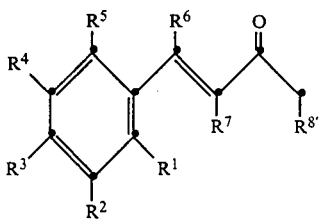

wherein $R^1$, $R^2$, $R^3$, $R^4$, $R^5$, $R^6$ and $R^7$ are as defined above and $R^{8'}$ is hydrogen or lower alkyl, with a compound of the formula

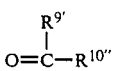

wherein $R^{9'}$ is hydrogen or lower alkyl and $R^{10''}$ is a group of formula (a) in which $R^{11}$ is hydrogen;

or (d) reacting a compound of the formula

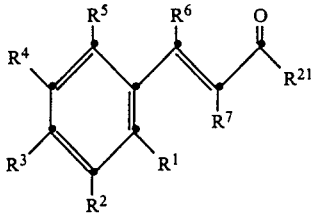

wherein $R^1$, $R^2$, $R^3$, $R^4$, $R^5$, $R^6$ and $R^7$ are as defined above and $R^{21}$ is a leaving group, with a compound of the formula

wherein $R^{10'''}$ is a group of formula (a), (b), (d), (e) or (f);

or (e) reacting a compound of the formula

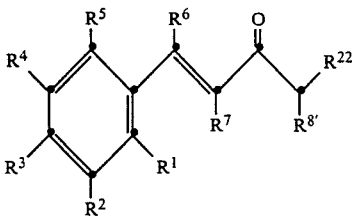

wherein $R^1$, $R^2$, $R^3$, $R^4$, $R^5$, $R^6$, $R^7$ and $R^{8'}$ are as defined above and $R^{22}$ is halogen, with a compound of the formula $$(R^{23})_3P=CH-R^{10iv} \qquad VIII$$

wherein $R^{23}$ is an aryl group and $R^{10iv}$ is a group of formula (a), (b), (d), (e) or (f), but in which $R^{11}$ and $R^{20}$ are not hydrogen;

or (f) cleaving off the protecting group(s) from a compound of the formula

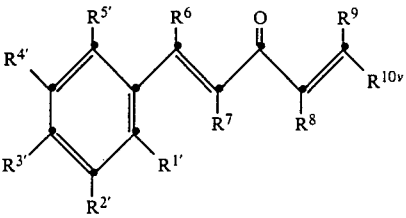

wherein $R^{1'}$, $R^{2'}$, $R^{3'}$, $R^{4'}$ and $R^{5'}$ are as defined above for $R^1$, $R^2$, $R^3$, $R^4$ and $R^5$ and a maximum of three of these can additionally represent protected hydroxy, protected amino or protected lower alkylamino, $R^6$, $R^7$, $R^8$ and $R^9$ are as defined above, $R^{10v}$ is a group of formula (a), (b), (c), (d), (e) or $$-C(R^{18})(R^{19})OR^{20''} \qquad (f'')$$

in which $R^{18}$ and $R^{19}$ are as defined above and $R^{20''}$ has the meaning given above for $R^{20}$ and can additionally represent a protecting group, whereby the molecule contains at least one protecting group;

or (g) hydrolyzing a compound of formula I in which $R^{10}$ is a group of formula (a) in which $R^{11}$ is different from hydrogen, to the corresponding carboxylic acid; or (h) acylating a compound of formula I in which $R^{10}$ is a group of formula (f) in which $R^{20}$ is hydrogen; or (i) converting a compound of formula I in which $R^8$ and $R^9$ together represent an additional carbon-carbon bond and $R^{10}$ is a group of formula (d) in which $R^{15}$ is hydrogen, into the corresponding compound of formula I in which $R^8$ and $R^9$ are hydrogen, $R^{10}$ is a group of formula (a) and $R^{11}$ is hydrogen; or (j) converting a compound of formula I in which $R^{10}$ is a group of formula (d), into the corresponding compound of formula I in which $R^{10}$ is a group of formula (c); or (k) converting an acidic compound of formula I into a pharmaceutically acceptable salt with a base, or converting a basic compound of formula I into a pharmaceutically acceptable salt with an acid.

The compounds of formula II above are novel and constitute a further aspect of the present invention, as is a process for their preparation, which comprises reacting a compound of the formula

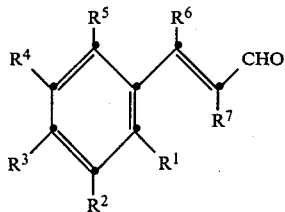 X wherein $R^1$, $R^2$, $R^3$, $R^4$, $R^5$, $R^6$ and $R^7$ are as defined above,
with a compound of the formula

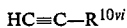 XI wherein $R^{10vi}$ is a group of formula (a), (b), (d), (e) or (f').

The compounds of formula II have similar pharmacodynamic properties to the styryl ketones of formula I, primarily those in which $R^{10'}$ is a group of formula (a), especially those in which $R^{11}$ is lower alkyl or lower alkoxy-lower alkoxy-lower alkyl. Representative examples of such compounds of formula II are methyl (E)-4-hydroxy-6-(4-methoxyphenyl)-5-hexen-2-ynoate and 2-(2-methoxyethoxy)ethyl (E)-4-hydroxy-6-(4-methoxyphenyl)-5-hexen-2-ynoate.

The present invention thus also encompasses compounds of general formula II as therapeutically active substances, medicaments containing them, and the use of the compounds of formula II in the control or prevention of illnesses, especially in the control or prevention of gastric ulcers or duodenal ulcers.

Process variant (a), above, yields styryl ketones of formula I in which $R^8$ and $R^9$ together represent an additional carbon-carbon bond and $R^{10}$ is a group of formula (a), (b), (d), (e) or (f').

The oxidation in accordance with process variant (a) is effected under methods which are known and familiar to those skilled in the art of converting a hydroxy group into an oxo group. As the oxidation agent there is conveniently used manganese dioxide (pyrolusite) in a suitable solvent which is inert under the reaction conditions, for example, a halogenated hydrocarbon such as methylene chloride or the like. The oxidation by means of manganese dioxide is conveniently effected in a temperature range of about 0° to about room temperature and takes about 10 minutes to about 20 hours, depending on the other conditions.

Process variant (b) yields styryl ketones of formula I in which $R^8$ and $R^9$ are hydrogen and $R^{10}$ is a group of formula (a), but in which $R^{11}$ is different from hydrogen. As the base there can be used a bicyclic nitrogen compound such as 1,8-diazabicyclo[5.4.0]undec-7-ene or 1,9-diazabicyclo[4.3.0]non-5-ene or the like. The reaction is effected in an organic solvent inert under the reaction conditions, for example, a halogenated hydrocarbon such as methylene chloride or the like. The reaction temperature preferably lies in a range around 0° C., and the reaction time is about 20 to 50 hours, e.g., 35 hours.

Process aspect (c) yields styryl ketones of formula I in which $R^8$ and $R^9$ are hydrogen or lower alkyl and $R^{10}$ is a group of formula (a) in which $R^{11}$ is hydrogen, i.e., carboxylic acids. As the compound of formula IV there is used, for example, glyoxylic acid which is conveniently employed in the form of the monohydrate. The reaction of the compounds of formulae III and IV is conveniently effected under acidic conditions, for example, in acetic acid or the like. The reaction is conveniently carried out at an elevated temperature, for example, at the reflux temperature of the reaction system, and it takes about 10 to about 30 hours, e.g., about 20 hours.

Process aspect (d) yields styryl ketones of formula I in which $R^8$ and $R^9$ together represent an additional carbon-carbon bond and $R^{10}$ is a group of formula (a), (b), (d), (e) or (f). As leaving groups ($R^{21}$) in the compounds of formula V used as starting materials, N-methoxy-N-methylamino or the like can be used. The reaction of the compounds of formulae V and VI is effected in the presence of a strong base such as n-butyllithium, alkylmagnesium halides (e.g., ethylmagnesium bromide) or the like, in an organic solvent or solvent mixture which is inert under the reaction conditions, such as tetrahydrofuran/n-hexane or the like. The reaction temperature depends, inter alia, on the base and the solvent system which are used, and it preferably lies in a range of about −100° C. to about 0° C. The reaction time amounts to about 5 to about 60 (for example, about 10 to about 30) minutes.

Process aspect (e) yields styryl ketones of formula I in which $R^8$ and $R^9$ are hydrogen and $R^{10}$ is a group of formula (a), (b), (d), (e) or (f), but in which $R^{11}$ and $R^{20}$, respectively, are different from hydrogen. The reaction of the compounds of formulae VII and VIII is conveniently effected in an organic solvent which is inert under the reaction conditions, for example, in an aromatic hydrocarbon such as toluene or the like, etc. The reaction temperature depends, inter alia, on the nature of the compounds of formulae VII and VIII which are used as well as on the solvent. The reaction is conveniently carried out at an elevated temperature, for example, at the reflux temperature of the reaction system. The reaction time amounts to about 1 to about 5 (for example, 2) hours.

Suitable protecting groups in the compounds of general formula IX which are used as starting materials in process variant (f) are, of course, only those which can be cleaved off by methods which selectively remove these protecting groups without affecting other structural elements present in the molecule. The removal of the protecting group or protecting groups from the compounds of formula IX is effected according to known methods, in which the nature of the protecting group or protecting groups must be taken into consideration when choosing the method to be used and care must be taken that only the protecting group or groups is/are selectively removed without affecting other structural elements present in the molecule. Suitable O-protecting groups are, for example, readily cleavable acetal and ketal protecting groups such as methoxymethyl, methoxyethoxymethyl, 1-ethoxyethyl, 2-(trimethylsilyl)ethoxymethyl, tetrahydro-2H-pyran-2-yl and the like; readily cleavable metal-organic groups, especially trialkylsilyl groups such as trimethylsilyl, t-butyldimethylsilyl and the like; readily cleavable aralkyl groups such as triphenylmethyl and the like; and readily cleavable acyl groups such as acetyl and the like; Suitable N-protecting groups are primarily readily cleavable acyl groups such as t-butyloxycarbonyl and the like.

Methods for the removal of the groups which have been mentioned hereinbefore as examples of protecting groups are described in the literature and are, accordingly, familiar to those skilled in the art. Thus, for example, the methoxymethyl group, the methoxyethoxymethyl group, the 1-ethoxyethyl group, the 2-(trimethylsilyl)ethoxymethyl group, the tetrahydro-2H-pyran-2-yl group, the trimethylsilyl group, the t-butyldimethylsilyl group and the triphenylmethyl group can be cleaved off under acidic conditions, for example, by means of aqueous hydrochloric acid in an organic solvent which is inert under the reaction conditions, such as tetrahydrofuran. The tetrahydro-2H-pyran-2-yl group, the trimethylsilyl group and the t-butyldimethylsilyl group can, however, also be cleaved off conveniently by means of pyridinium p-toluene-sulphonate in an organic solvent or solvent mixture which is inert under the reaction conditions, such as tetra-hydrofuran/ethanol. The trimethylsilyl group and the t-butyldimethylsilyl group can also be cleaved off by means of a quaternary ammonium fluoride such as tetrabutylammonium fluoride in an organic solvent which is inert under the reaction conditions, such as tetrahydrofuran. The acetyl group can be cleaved off under mild alkaline conditions, for example, by means of dilute (about 2-5%) potassium hydroxide solution in an organic solvent which is inert under the reaction conditions, such as tetrahydrofuran. The cleavage of a t-butyloxycarbonyl group can be effected under acidic conditions, e.g., by means of an aqueous acid or anhydrous trifluoroacetic acid.

The hydrolysis in accordance with process variant (g) is effected according to methods which are known and familiar to those skilled in the art, such as by means of a strong inorganic base, for example, an alkali metal hydroxide such as potassium hydroxide or the like, in a suitable solvent system, for example, water or aqueous tetrahydrofuran and the like.

The acylation in accordance with process variant (h) is also effected according to known methods. As the acylation agent there is used, for example, an acid halide which corresponds to the acyl residue to be introduced, such as acetyl chloride, 3,4,5-trimethoxybenzoyl chloride and the like. The acylation by means of such an acid halide is conveniently effected in the presence of a base, especially a tertiary organic base such as pyridine, triethylamine, N-methylpiperidine, 4-dimethylaminopyridine or the like. Suitable solvents are primarily halogenated hydrocarbons such as methylene chloride or the like. When pyridine is used as the base, then this can simultaneously also serve as the solvent. If one or more of $R^1$–$R^5$ signifies a hydroxy group and/or an amino group and/or a lower alkylamino group, they are likewise acylated.

Process variant (i) is effected under acidic conditions, conveniently in the presence of aqueous acid, for example, aqueous hydrobromic acid or the like, in a water-miscible organic solvent which is inert under the reaction conditions, such as dioxane or the like. The reaction temperature is usually about 10° to about 50° C. (for example, about 30° C.) and the reaction time usually amounts to from about 10 to about 30 (for example, about 18) hours.

In accordance with process variant (j) an acetal or ketal group is converted into a carbonyl group. This is effected according to methods which are familiar to those skilled in the art, conveniently by means of aqueous perchloric acid or the like, in an organic solvent which is inert under the reaction conditions, such as dioxane or the like, at about room temperature, for a few (for example, 2) hours.

The conversion of an acidic compound of formula I into a pharmaceutically acceptable salt can be carried out by treatment with a suitable base in a known manner. As such salts there are suitable not only those with cations derived from an inorganic base, e.g., potassium salts, sodium salts, calcium salts and the like, but also salts with organic bases such as ethylenediamine, monoethanolamine, diethanolamine and the like.

The conversion of a basic compound of formula I into a pharmaceutically acceptable salt can be carried out by treatment with a suitable acid. As such salts there are suitable not only those with inorganic acids, such as hydrogen chloride, hydrogen bromide, phosphoric acid, sulphuric acid and the like, but also salts with organic acids, such as citric acid, malic acid, methanesulphonic acid, p-toluenesulphonic acid and the like.

The preparation of compounds of formula II from compounds of formulae X and XI is effected in the presence of a strong base such as n-butyllithium, alkylmagnesium halides (e.g., ethylmagnesium bromide) or the like, in an organic solvent or solvent mixture which is inert under the reaction conditions, such as tetrahydrofuran/n-hexane and the like. The reaction temperature depends, inter alia, on the nature of the starting materials of formulae X and XI which are used, as well as the base and solvent or solvent mixture which are used. The reaction temperature is usually in the range of about −110° to about 0° C., especially about −80° to −70° (for example, at about 78°) C. The reaction time varies from a few minutes to several hours, for example from about 5 minutes to about 2 hours, depending on the other reaction conditions.

The starting materials of formula III can be prepared, for example, by reacting compounds of the formula

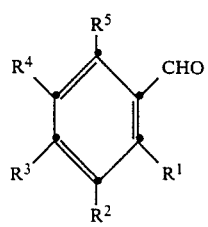 XII wherein $R^1$, $R^2$, $R^3$, $R^4$ and $R^5$ are as defined above, with a compound of the formula $$R^7-CH_2-CO-CH_2-R^{8'} \quad\quad XIII$$

wherein $R^7$ and $R^{8'}$ are as defined above,
according to known methods. Moreover, various Examples hereinafter contain detailed information concerning the preparation of compounds of formula III.

The starting materials of formula IV are available or can be prepared readily according to methods which are known and familiar to those skilled in the art.

Starting materials of formula V can be prepared according to methods which are known and familiar to those skilled in the art from corresponding compounds of the formula

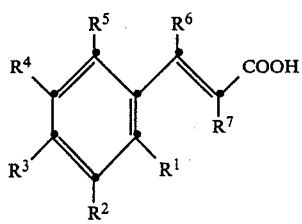

wherein $R^1$, $R^2$, $R^3$, $R^4$, $R^5$, $R^6$ and $R^7$ are as defined above.

Compounds of formula V in which $R^{21}$ is N-methoxy-N-methylamino are obtained, for example, by reacting compounds of formula XIV with N,O-dimethylhydroxylamine in the presence of dicyclohexylcarbodiimide or the like, in an organic solvent which is inert under the reaction conditions, for example, a halogenated hydrocarbon such as methylene chloride or the like. Various Examples hereinafter contain detailed information concerning the preparation of compounds of formula V.

The starting materials of formula VI are available or are readily prepared according to methods which are known and familiar to any person skilled in the art. Various Examples hereinafter contain detailed information concerning the preparation of compounds of formula VI.

Compounds of formula VII can be prepared, for example, from corresponding compounds of formula III by reaction with a suitable halogenating agent such as 5,5-dibromobarbituric acid or the like.

Compounds of formula VIII can be prepared, for example, by reacting a compound of the formula $$R^{22}-CH_2-R^{10iv} \quad\quad XV$$

wherein $R^{22}$ and $R^{10iv}$ are as defined above,
with a triarylphosphine such as triphenylphosphine or the like (for example, in an aromatic hydrocarbon such as toluene or the like, at about room temperature, the reaction taking about 4 hours), whereupon the desired corresponding phosphorane of formula VIII is obtained by treating the resulting phosphonium halide with a base (e.g., with aqueous sodium hydroxide solution or the like).

The preparation of compounds of formula IX can be effected by analogy to methods for the preparation of corresponding styryl ketones of formula I.

The compounds of formulae X, XI, XII, XIII, XIV and XV are available or can be prepared readily according to methods which are know and familiar to those skilled in the art.

As mentioned earlier, the compounds of general formulae I and II as well as pharmaceutically acceptable salts of compounds of formula I possess valuable pharmacodynamic properties.

Representative compounds of formulae I and II have been investigated with respect to their mucosa-protective and gastric acid secretion-inhibiting properties as well as to their toxicity.

The experimental procedure described hereinafter has been used to determine the mucosa-protective property:

The oral administration of absolute ethanol to male rats in a dosage of 1 ml per rat leads within 1 hour to bloody lesions of the mucous membrane of the stomach. Various dosages of the substances to be tested (suspended in 0.125% carboxymethylcellulose) or of the vehicle alone (control) are administered to the rats orally (1 ml per rat) 30 minutes prior to the treatment with ethanol. One hour after the administration of the ethanol the animals are sacrificed, their stomachs are examined for the presence of lesions, and the number and size of such lesions are mentioned. The $ID_{50}$ is that dosage of a test substance which reduces by 50% the number of lesions in comparison to the control group.

The test procedure described hereinafter was used to determine the gastric acid secretion-inhibiting activity:

The pylorus of male rats is ligated under slight ether narcosis in accordance with the procedure described by Shay et al. in Gastroenterology 5, 43 (1945). The substances to be tested, suspended in 0.5% carboxymethylcellulose, are administered intraduodenally. Control animals are treated only with the vehicle. Five hours after the ligation the animals are sacrificed, the volume and acidity of their gastric fluid are determined, and the values obtained are compared with those of control animals. The $ID_{50}$ is that dosage of a test substance which brings about a 50% decrease of the secretion in comparison to the control animals.

In the following Table there are given for a series of representative compounds of formula I and for two compounds of formula II the results of the testing with respect to their mucosa-protective activity ("ethanol test") and to their gastric acid secretion-inhibiting activity. Moreover, this Table contains data concerning the acute toxicity ($LD_{50}$ in the case of single oral administration to mice).

| Compound | Ethanol Test ID 50 mg/kg p.o. | Gastric acid secretion-inhibition ID 50 mg/kg i.d. | Toxicity LD 50 mg/kg p.o. |
| --- | --- | --- | --- |
| A | 0.8 | 9 | 312–625 |
| B | 0.7 | — | 312–625 |
| C | 1.0 | — | 625–1250 |
| D | 0.5 | — | 500–1000 |
| E | 1.9 | — | 312–625 |
| F | 0.7 | — | 156–312 |
| G | 2.7 | — | 500–1000 |
| H | 2.7 | — | 2500–5000 |
| I | 2.1 | — | 1000–2000 |

-continued

| Compound | Ethanol Test ID 50 mg/kg p.o. | Gastric acid secretion-inhibition ID 50 mg/kg i.d. | Toxicity LD 50 mg/kg p.o. |
|---|---|---|---|
| J | 3.4 | — | >4000 |

A = (E,E)-6-(3-Methoxyphenyl)-4-oxo-2,5-hexadienoic acid
B = (E,E)-6-(4-Methoxyphenyl)-4-oxo-2,5-hexadienoic acid
C = Methyl (2Z,5E)-6-(4-methoxyphenyl)-4-oxo-2,5-hexadienoate
D = (E)-6-(4-Methoxyphenyl)-4-oxo-5-hexen-2-ynoic acid
E = (E,E)-6-(4-Fluorophenyl)-4-oxo-2,5-hexadienoic acid
F = (2Z,5E)-6-(4-Methoxyphenyl)-4-oxo-2,5-hexadienoic acid
G = 2-(2-Methoxyethoxy)ethyl (E,E)-6-(3-methoxyphenyl)-4-oxo-2,5-hexadienoate
H = 2-(2-Methoxyethoxy)ethyl (E)-6-(4-methoxyphenyl)-4-oxo-5-hexen-2-ynoate
I = Methyl (E)-4-hydroxy-6-(4-methoxyphenyl)-5-hexen-2-ynoate
J = 2-(2-Methoxyethoxy)ethyl (E)-4-hydroxy-6-(4-methoxy-phenyl)-5-hexen-2-ynoate.

The compounds of formulae I and II and the pharmaceutically acceptable salts of compounds of formula I can be used as medicaments, such as in the form of pharmaceutical preparations. Administration can be effected orally in the form of solid pharmaceutical preparations such as tablets, coated tablets, dragees, hard gelatine capsules and soft gelatine capsules. Oral administration in the form of liquid preparations such as solutions, emulsions and suspensions, rectal administration, for example, in the form of suppositories, or parenteral administration, for example, in the form of injection solutions, is also possible.

Such pharmaceutical compositions, containing a compound of formula I or II or a pharmaceutically acceptable salt of a compound of formula I, are also an aspect of the present invention. The preparation of such compositions can be effected by mixing one or more of the compounds of formula I or II, or of the pharmaceutically acceptable salts of the compounds of formula I and, if desired, one or more other therapeutically active substances into a suitable dosage form together with one or more therapeutically inert excipients.

For the preparation of tablets, coated tablets, dragees and hard gelatine capsules, the compounds of formulae I and II and the pharmaceutically acceptable salts of compounds of formula I can be processed with pharmaceutically inert, inorganic or organic excipients. As such excipients there can be used in the case of tablets, dragees and hard gelatine capsules such materials as lactose, maize starch or derivatives thereof, talc, stearic acid or its salts, and so forth. For the preparation of pharmaceutical preparations which are resistant to gastric fluid, it is necessary to apply a gastric fluid-resistant (enteric) coating, which, for instance, can consist of hydroxypropylmethylcellulose phthalate, or other suitable material the selection of which is within the ability of those skilled in the art.

Suitable excipients for soft gelatine capsules are, for example, vegetable oils, waxes, fats, semi-solid and liquid polyols, and so forth.

Suitable excipients for solutions and syrups are, for example, water, polyols, saccharose, invert sugar, glucose and the like.

Suitable excipients for suppositories are, for example, natural or hardened oils, waxes, fats, semi-liquid or liquid polyols and the like.

Suitable excipients for injection solutions are, for example, water, alcohols, polyols, glycerine, vegetable oils, and so forth.

The pharmaceutical preparations can contain, in addition, preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically useful substances, as those skilled in the art will appreciate.

In accordance with this invention, the compounds of formulae I and II and the pharmaceutically acceptable salts of compounds of formula I can be used in the control or prevention of certain illnesses, especially in the control or prevention of gastric ulcers and/or duodenal ulcers. The dosage can vary within wide limits and, of course, will be fitted to the individual requirements in each particular case. In general, in the case of oral administration a daily dosage of about 30–400 mg, singly or in divided amounts, will be appropriate and in the case of intravenous administration a daily dosage of about 1–50 mg will be appropriate.

In the following Examples, which illustrate the present invention but which are not intended to be limiting, all temperatures are given in degrees Celsius.

EXAMPLE 1

(a) A solution of 19.6 g (0.1 mol) of 2,3,4-trimethoxybenzaldehyde in 21 ml (0.28 mol) of acetone and 10.5 ml of water was treated with 2.5 ml of 3N sodium hydroxide solution, whereby the temperature of the reaction mixture should not exceed 30°. The mixture was stirred at room temperature for 20 hours, diluted with water, and 3N hydrochloric acid was added to produce a strongly acidic reaction. The aqueous phase was extracted twice with methylene chloride. The combined organic phases were washed with water, dried over magnesium sulphate and concentrated. The residue was purified by flash chromatography on 1000 g of silica gel (elution agent ether/hexane 10:1). There was obtained (E)-4-(2,3,4-trimethoxyphenyl)but-3-en-2-one as a yellow oil. MS: 236 (M+), 205 (base peak) m/e.

(b) A solution of 18 g (76 mmol) of (E)-4-(2,3,4-trimethoxyphenyl)but-3-en-2-one and 7 g (76 mmol) of glyoxylic acid monohydrate in 19 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from ether/methylene chloride yielded (E,E)-4-oxo-6-(2,3,4-trimethoxyphenyl)-2,5-hexadienoic acid of melting point 125°–127°.

EXAMPLE 2

A solution of 21.5 g (131 mmol) of (E)-4-(4-fluorophenyl-but-3-en-2-one and 12 g (131 mmol) of glyoxylic acid monohydrate in 32 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from ethyl acetate/ether yielded (E,E)-6-(4-fluorophenyl)-4-oxo-2,5-hexadienoic acid of melting point 160°–162°.

EXAMPLE 3

A solution of 10.5 g (54.6 mmol) of (E)-4-[4-(methylthio)phenyl]but-3-en-2-one and 5.02 g (54.6 mmol) of glyoxylic acid monohydrate in 15 ml of acetic acid was heated at reflux for 20 hours. The reaction mixture was diluted with water and extracted with methylene chloride. The organic phase was extracted twice with 3N sodium hydroxide solution. The combined aqueous phases were treated with 3N hydrochloric acid to produce a strongly acidic reaction and extracted twice with methylene chloride. The combined organic phases were dried over magnesium sulphate and concentrated. Crystallization of the residue from methylene chloride/ether yielded (E,E)-6-[4-(methylthio)-phenyl]-4-oxo-2,5-hexadienoic acid of melting point 160°–163°.

EXAMPLE 4

A solution of 19 g (92 mmol) of (E)-4-(2,4-dimethoxyphenyl)but-3-en-2-one and 8.4 g (92 mmol) of glyoxylic acid monohydrate in 24 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from methylene chloride/ether/hexane yielded (E,E)-6-(2,4-dimethoxyphenyl)-4-oxo-2,5-hexadienoic acid of melting point 195°–200°.

EXAMPLE 5

A solution of 17 g (96 mmol) of (E)-4-(4-methoxyphenyl)but-3-en-2-one and 8.9 g (96 mmol) of glyoxylic acid monohydrate in 25 ml of glacial acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from methylene chloride/ether/hexane yielded (E,E)-6-(4-methoxyphenyl)-4-oxo-2,5-hexadienoic acid of melting point 138°–139°.

EXAMPLE 6

A solution of 14.7 g (83.4 mmol) of (E)-4-(3-methoxyphenyl)but-3-en-2-one and 7.67 g (83.4 mmol) of glyoxylic acid monohydrate in 21.2 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from ether/ethyl acetate yielded (E,E)-6-(3-methoxyphenyl)-4-oxo-2,5-hexadienoic acid of melting point 158°–160°.

EXAMPLE 7

A solution of 5 g (21 mmol) of (E)-4-(3,4,5-trimethoxyphenyl)but-3-en-2-one and 2 g (21.7 mmol) of glyoxylic acid monohydrate in 5.2 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from methylene chloride/ether yielded (E,E)-4-oxo-6-(3,4,5-trimethoxyphenyl)-2,5-hexadienoic acid of melting point 152°–154°.

EXAMPLE 8

A solution of 15 g (78.8 mmol) of (E)-4-[3,4-(methylenedioxy)phenyl]but-3-en-2-one and 7.2 g (78.8 mmol) of glyoxylic acid monohydrate in 20 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from ethyl acetate/ether yielded (E,E)-6-[3,4-(methylenedioxy)phenyl]-4-oxo-2,5-hexadienoic acid of melting point 170°–173°.

EXAMPLE 9

A solution of 12 g (56 mmol) of (E)-4-(4-trifluoromethylphenyl)but-3-en-2-one and 5.15 g (56 mmol) of glyoxlic acid monohydrate in 14 ml of acetic acid was heated at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from ether/hexane yielded (E,E)-4-oxo-6-(4-trifluoromethylphenyl)-2,5-hexadienoic acid of melting point 192°–195°.

EXAMPLE 10

(a) A solution of 16.6 g (0.1 mol) of 2,5-dimethoxybenzaldehyde in 21 ml (0.28 mol) of acetone and 10 ml of water was treated with 2.5 ml of 3N sodium hydroxide solution. The temperature of the reaction mixture should not exceed 30°. The mixture was stirred at room temperature for 20 hours, diluted with water and 3N hydrochloric acid was added to produce a strongly acidic reaction. The aqueous phase was extracted twice with methylene chloride. The combined organic phases were washed with water, dried over magnesium sulphate and concentrated. The residue was purified by flash chromatography on 1000 g of silica gel (elution agent methylene chloride/ethyl acetate 9:1). There was obtained (E)-4-(2,5-dimethoxyphenyl)but-3-en-2-one as a yellow oil.

MS: 206 (M+) m/e.

(b) A solution of 19 g (92 mmol) of (E)-4-(2,5-dimethoxyphenyl)but-3-en-2-one and 8.4 g (92 mmol) of glyoxylic acid monohydrate in 23.4 ml of acetic acid was boiled at reflux for 20 hours. The reaction mixture was diluted with water and extracted with ethyl acetate. The organic phase was extracted twice with 3N sodium hydroxide solution. The combined aqueous phases were treated with 3N hydrochloric acid to produce a strongly acidic reaction and extracted twice with ethyl acetate. The combined organic phases were dried over magnesium sulphate and concentrated. Crystallization of the residue from ether/ethyl acetate yielded (E,E)-6-(2,5-dimethoxyphenyl)-4-oxo-2,5-hexadienoic acid of melting point 145°–146°.

EXAMPLE 11

(a) A solution of 20 g (0.36 mol) of 2-propyn-1-ol in 637 ml (6.66 mol) of ethyl vinyl ether was treated at 0° under argon with 1.27 ml (16.7 mmol) of trifluoroacetic acid and the mixture was subsequently stirred at room temperature for 65 hours. 1.3 g of sodium carbonate were added, the reaction mixture was stirred at room temperature for a further 30 minutes and concentrated on a rotary evaporator. Distillation of the residue under reduced pressure yielded 1-(1-ethoxyethoxy)-2-propyne of boiling point 55°/30 mmHg.

MS: 127 (M—H) m/e.

(b) A solution of 34.74 g (168 mmol) of dicyclohexylcarbodiimide in 300 ml of methylene chloride was treated at −10° with a solution of 10.3 g (168 mmol) of N,O-dimethylhydroxylamine in 100 ml of methylene chloride. The mixture was stirred at −10° for a further 10 minutes and then a solution of 30 g (168 mmol) of 4-methoxycinnamic acid in 100 ml of methylene chloride was added rapidly. The mixture was stirred at room temperature for a further 20 hours and it was then treated with 200 ml of 3N ammonia solution and extracted twice with 200 ml of methylene chloride each time. The combined organic phases were dried over magnesium sulphate and concentrated. The residue was purified by flash chromatography on 1000 g of silica gel (elution agent methylene chloride/ethyl acetate 9:1). There was obtained 4-methoxycinnamic acid N,O-dimethylhydroxamate as a yellow oil.

MS: 221 (M+), 161 (base peak) m/e.

(c) A solution of 5.18 g (40 mmol) of 1-(1-ethoxyethoxy)-2-propyne in 100 ml of tetrahydrofuran was treated at −78° under argon with 25 ml of n-butyllithium solution (1.6M in hexane). The mixture was stirred at −40° for 30 minutes, again cooled to −78° and a solution of 8.85 g (40 mmol) of 4-methoxycinnamic acid N,O-dimethylhydroxamate in 100 ml of tetrahydrofuran was added. The reaction mixture was stirred at −78° for a further 10 minutes, then warmed to 0° and treated with 100 ml of saturated ammonium chloride solution. The aqueous phase was extracted twice with ether. The combined organic phases were washed successively with saturated sodium chloride solution and with water, dried over sodium sulphate and concentrated. The residue was purified by flash chromatography on 500 g of silica gel (elution agent methylene chloride/ether 4:1). There was obtained (E)-6-(1-ethoxy-ethoxy)-1-(4-methoxyphenyl)-1-hexen-4-yn-3-one as a red oil.

MS: 288 (M+), 45 (base peak) m/e.
IR (film): 2217, 1629, 1599, 1512, 1249 cm$^{-1}$.

EXAMPLE 12

(a) A solution of 20.6 g (0.1 mol) of dicyclohexylcarbodiimide in 250 ml of methylene chloride was treated at −10° with a solution of 6.1 g (0.1 mol) of N,O-dimethylhydroxylamine in 100 ml of methylene chloride. The mixture was stirred at −10° for a further 10 minutes and then a solution of 23 g (0.1 mol) of 3,4,5-trimethoxycinnamic acid in 100 ml of methylene chloride was added rapidly. The mixture was stirred at room temperature for a further 20 hours and then treated with 200 ml of 3N ammonia solution and extracted twice with 200 ml of methylene chloride each time. The combined organic phases were dried over magnesium sulphate and concentrated. The residue was purified by flash chromatography on 1000 g of silica gel (elution agent methylene chloride/ether 4:1) and subsequently crystallized from ether. There was obtained 3,4,5-trimethoxycinnamic acid N,O-dimethylhydroxamate.

MS: 281 (M+), 221 (base peak) m/e.

(b) A solution of 5.18 g (40 mmol) of 1-(1-ethoxyethoxy)-2-propyne in 100 ml of tetrahydrofuran was treated at −78° under argon with 25 ml of n-butyllithium solution (1.6M in hexane). The mixture was stirred at −40° for 30 minutes, again cooled to −78° and a solution of 11.25 g (40 mmol) of 3,4,5-trimethoxycinnamic acid N,O-dimethylhydroxamate in 100 ml of tetrahydrofuran was added. The reaction mixture was stirred at −78° for a further 10 minutes, then warmed to 0° and treated with 100 ml of saturated ammonium chloride solution. The aqueous phase was extracted twice with ether. The combined organic phases were washed in succession with saturated sodium chloride solution and with water, dried over sodium sulphate and concentrated. The residue was purified by flash chromatography on 500 g of silica gel (elution agent methylene chloride/ether 4:1). There was obtained (E)-6-(1-ethoxy-ethoxy)-1-(3,4,5-trimethoxyphenyl)-1-hexen-4-yn-3-one as a brown oil.

MS: 348 (M+), 45 (base peak) m/e.

EXAMPLE 13

A solution of 3 g (10.4 mmol) of (E)-6-(1-ethoxyethoxy)-1-(4-methoxyphenyl)-1-hexen-4-yn-3-one in 50 ml of tetrahydrofuran was treated at room temperature with 3 ml of 1N hydrochloric acid and stirred at room temperature for 30 minutes. The reaction mixture was diluted with water and extracted twice with ether. The combined organic phases were dried over magnesium sulphate and concentrated. The residue was purified by flash chromatography on 100 g of silica gel (elution agent methylene chloride/ether 4:1) and was subsequently crystallized from methylene chloride/ether/hexane. There was obtained (E)-6-hydroxy-1-(4-methoxyphenyl)-1-hexen-4-yn-3-one of melting point 68°–69°.

EXAMPLE 14

A solution of 4 g (11.5 mmol) of (E)-6-(1-ethoxyethoxy)-1-(3,4,5-trimethoxyphenyl)-1-hexen-4-yn-3-one in 40 ml of ethanol/tetrahydrofuran (1:1) was treated at room temperature with 0.4 g (1.6 mmol) of pyridinium (toluene-4-sulphonate) and was stirred at room temperature for 20 hours. The reaction mixture was diluted with water and extracted twice with ether. The combined organic phases were dried over magnesium sulphate and concentrated. The residue was purified by flash chromatography on 200 g of silica gel (elution agent methylene chloride/ether 4:1) and was subsequently crystallized from methylene chloride/ether. There was obtained (E)-6-hydroxy-1-(3,4,5-trimethoxyphenyl)-1-hexen-4-yn-3-one of melting point 113°–115°.

EXAMPLE 15

(a) A solution of 6.5 ml (0.11 mol) of 2-propyn-1-ol in 80 ml of tetrahydrofuran was treated at −78° under argon with 13.5 g (0.12 mol) of potassium tert.-butylate. The mixture was stirred at −78° for 3 hours, 14.1 ml (0.12 mol) of 3,3-dimethylallyl bromide were then added and the mixture was again stirred at −78° for 3 hours and at room temperature for 20 hours. The reaction mixture was poured into ice/water and extracted twice with ether. The combined organic phases were dried over magnesium sulphate and concentrated. There was obtained 1-[(3-methyl-2-butenyl)oxy]-2-propyne as a yellow oil which is processed without purification.

MS: 123 (M—H), 109 (M—CH$_3$) m/e.

(b) A solution of 4.97 g (40 mmol) of 1-[(3-methyl-2-butenyl)oxy]-2-propyne in 100 ml of tetrahydrofuran was treated at −78° under argon with 25 ml of a n-butyllithium solution (1.6M in hexane). The mixture was stirred at −40° for 30 minutes, again cooled to −78° and then a solution of 8.85 g (40 mmol) of 4-methoxycinnamic acid N,O-dimethylhydroxamate in 100 ml of tetrahydrofuran was added. The reaction mixture was stirred at −78° for a further 10 minutes, then warmed to 0° and treated with 100 ml of saturated ammonium chloride solution. The aqueous phase was extracted twice with ether. The combined organic phases were washed in succession with saturated sodium chloride solution and with water, dried over magnesium sulphate and concentrated. The residue was purified by flash chromatography on 700 g of silica gel (elution agent methylene chloride/ether 4:1). There was obtained (E)-1-(4-methoxyphenyl)-6-[(3-methyl-2-butenyl)-oxy]-1-hexen-4-yn-3-one as a brown oil.

MS: 284 (M+), 161 (base peak) m/e.

IR (film): 2214, 1628, 1599, 1512, 1248, 1173, 1078, 1028 cm$^{-1}$.

EXAMPLE 16

(a) A solution of 41.26 g (0.2 mol) of dicyclohexylcarbodiimide in 250 ml of methylene chloride was treated at −10° with a solution of 12.2 g (0.2 mol) of N,O-dimethylhydroxylamine in 250 ml of methylene chloride. The mixture was stirred at −10° for a further 10 minutes and then a solution of 38.8 g (0.2 mol) of 4-hydroxy-3-methoxycinnamic acid in 250 ml of methylene chloride was added rapidly. The mixture was stirred at room temperature for a further 20 hours, treated with 500 ml of 3N ammonia solution and extracted twice with methylene chloride. The combined organic phases were dried over magnesium sulphate and concentrated. The residue was purified by flash chromatography on 1000 g of silica gel (elution agent methylene chloride/ether 4:1) and subsequently crystallized from methylene chloride/ether/hexane. There was obtained 4-hydroxy-3-methoxycinnamic acid N,O-dimethylhydroxamate of melting point 85°–86°.

(b) A solution of 7.6 g (61.7 mmol) of 1-[(3-methyl-2-butenyl)oxy]-2-propyne in 100 ml of tetrahydrofuran was treated at −78° under argon with 38.5 ml of n-butyllithium solution (1.6M in hexane). The mixture was left to stir at −40° for 30 minutes, again cooled to −78° and a solution of 7.3 g (30.8 mmol) of 4-hydroxy-3-methoxycinnamic acid N,O-dimethylhydroxamate in 50 ml of tetrahydrofuran was added. The reaction mixture was stirred at −78° for a further 30 minutes, then warmed to 0° and treated with 100 ml of saturated ammonium chloride solution. The aqueous phase was extracted twice with ether. The combined organic phases were washed in succession with saturated sodium chloride solution and with water, dried over magnesium sulphate and concentrated. The residue was purified by flash chromatography on 500 g of silica gel (elution agent methylene chloride/ether 4:1). There was obtained (E)-1-(4-hydroxy-3-methoxyphenyl)-6-[(3-methyl-2-butenyl)oxy]-1-hexen-4-yn-3-one as a red oil.

MS: 300 (M+), 177 (base peak) m/e.

IR (film): 3367, 2213, 1625, 1567, 1513 cm$^{-1}$.

EXAMPLE 17

(a) A solution of 5 ml (60 mmol) of methyl propiolate in 100 ml of tetrahydrofuran was treated at −78° under argon with 41.3 ml of n-butyllithium solution (1.6M in hexane). The mixture was stirred at −78° for 10 minutes and then a solution of 9.73 g (60 mmol) of 4-methoxycinnamaldehyde in 100 ml of tetrahydrofuran was added. The reaction mixture was stirred at −78° for 20 minutes, then warmed to −20° and treated with 100 ml of saturated ammonium chloride solution. The aqueous phase was extracted twice with ether. The combined organic phases were washed with water, dried over sodium sulphate and concentrated. Flash chromatography of the residue on 1000 g of silica gel (elution agent methylene chloride/ethyl acetate 9:1) yielded methyl (E)-4-hydroxy-6-(4-methoxyphenyl)-5-hexen-2-ynoate as a yellow oil.

MS: 246 (M+), 121 (base peak) m/e.

IR (film): 3400, 2950, 2236, 1716, 1606, 1518, 1435, 1252, 1031 cm$^{-1}$.

(b) A solution of 10.7 g (43.4 mmol) of methyl (E)-4-hydroxy-6-(4-methoxyphenyl)-5-hexen-2-ynoate in 150 ml of methylene chloride was added dropwise at 0° to a suspension of 56.7 g (652 mmol) of manganese dioxide in 200 ml of methylene chloride. The reaction mixture was stirred at 0° for 2 hours, filtered over magnesium sulphate and concentrated. Crystallization of the residue from ether yielded methyl (E)-6-(4-methoxyphenyl)-4-oxo-5-hexen-2-ynoate of melting point 70°.

EXAMPLE 18

A solution of 5.3 g (21.7 mmol) of methyl (E)-6-(4-methoxyphenyl)-4-oxo-5-hexen-2-ynoate in 70 ml of tetrahydrofuran was treated at 0° within 15 minutes with 48.6 ml (26 mmol) of a 3% aqueous potassium hydroxide solution. The reaction mixture was stirred at 0° for 10 minutes, then diluted with 100 ml of water and extracted once with 100 ml of ether. The organic phase was discarded. The aqueous phase was adjusted to pH 1 by the careful addition of 1N hydrochloric acid and extracted twice with ether. The combined organic phases were washed with water, dried over sodium sulphate and concentrated. Crystallization of the residue from ether/hexane yielded (E)-6-(4-methoxy-phenyl)-4-oxo-5-hexen-2-ynoic acid of melting point 98°–100°.

EXAMPLE 19

A solution of 20 g (8.12 mmol) of methyl (E)-4-hydroxy-6-(4-methoxyphenyl)-5-hexen-2-ynoate and 62 mg (∼5 mol %) of 2,8-diazabicyclo[5.4.0]undec-7-ene in 80 ml of methylene chloride was stirred at 0° under argon for 35 hours. Thereafter, 25 ml of 0.1N hydrochloric acid were added and the phases are separated. The aqueous phase was extracted twice with 25 ml of methylene chloride. The combined organic fractions were dried over magnesium sulphate, filtered and evaporated. The residue was chromatographed on 130 g of silica gel with petroleum ether/ether (1:1), and there were obtained first methyl (E,E)-6-(4-methoxyphenyl)-4-oxo-2,5-hexadienoate of melting point 103°–103.5° and then methyl (2Z,5E)-6-(4-methoxyphenyl)-4-oxo-2,5-hexadienoate of melting point 54°–55°.

EXAMPLE 20

A solution of 1.70 g (6.9 mmol) of methyl (2Z,5E)-6-(4-methoxyphenyl)-4-oxo-2,5-hexadienoate in 20 ml of ether was treated while cooling with ice and stirring vigorously within about 15 minutes with 20 ml of 5% potassium hydroxide solution. The reaction mixture was stirred at 4° for 1 hour and then treated with 15 ml of phosphate buffer (pH=6.5) and 30 ml of ethyl acetate, whereupon the phases were separated. The aqueous phase was extracted twice with ethyl acetate. The combined organic phases were dried over magnesium sulphate, filtered and evaporated. The solid residue was recrystallized from ethyl acetate/hexane and there was obtained (2Z,5E)-6-(4-methoxyphenyl)-4-oxo-2,5-hexadienoic acid as an orange colored powder of melting point 103.5°–104°.

EXAMPLE 21

(a) 12.3 ml (0.2 mol) of propiolic acid are heated at reflux for 20 hours together with 23.6 ml (0.2 mol) of diethylene glycol monomethyl ether, 1.5 g (8 mmol) of p-toluenesulphonic acid monohydrate and 80 ml of toluene, and the resulting reaction water was distilled off azeotropically and collected in a water separator. After completion of the water separation the reaction mixture was washed in succession with saturated sodium bicarbonate solution and with water. The toluene phase was dried over sodium sulphate and concentrated. The crude product was purified by flash chromatography on 500 g of silica gel (elution agent methylene chloride/ethyl acetate 9:1). There was obtained 2-(2-methoxyethoxy)ethyl propiolate as a colorless oil.

(b) A solution of 1.75 g (10.2 mmol) of 2-(2-methoxyethoxy)ethyl propiolate in 20 ml of tetrahydrofuran was treated at −78° under argon with 7 ml of n-butyllithium solution (1.6M in hexane). The mixture was stirred at −78° for 5 minutes and then a solution of 1.65 g (10.2 mmol) of 4-methoxycinnamaldehyde in 25 ml of tetrahydrofuran was added within 10 minutes. The reaction mixture was stirred at −78° for 5 minutes and then treated with 50 ml of saturated ammonium chloride solution. The aqueous phase was extracted twice with ether. The combined organic phases were washed with water, dried over sodium sulphate, filtered and concentrated. Flash chromatography of the residue on 120 g of silica gel (elution agent methylene chloride/ether 4:1) yielded 2-(2-methoxyethoxy)ethyl (E)-4-hydroxy-6-(4-methoxyphenyl)-5-hexen-2-ynoate as a yellow oil.

MS: 334 (M+), 214, 186, 158, 59, 45 (base peak) m/e.
IR (film): 3395, 2236, 1713, 1606, 1512, 1252 cm$^{-1}$.

(c) A solution of 2.4 g (7.2 mmol) of 2-(2-methoxyethoxy)-ethyl (E)-4-hydroxy-6-(4-methoxyphenyl)-5-hexen-2-ynoate in 40 ml of methylene chloride was added dropwise at 0° to a suspension of 9.4 g (108 mmol) of manganese dioxide in 30 ml of methylene chloride. The reaction mixture was stirred at 0° for 2 hours, filtered over magnesium sulphate and concentrated. Crystallization of the residue from ether/hexane yielded 2-(2-methoxyethoxy)ethyl (E)-6-(4-methoxyphenyl)-4-oxo-5-hexen-2-ynoate of melting point 41°–42°.

EXAMPLE 22

(a) A solution of 13.9 g (0.1 mmol) of bromoacetic acid in 40 ml of toluene was treated with 11.8 ml (0.1 mol) of diethylene glycol monomethyl ether and 0.8 g of p-toluenesulphonic acid monohydrate. The mixture was heated under reflux on a water separator until water no longer separated. The reaction mixture was washed in succession with water, saturated sodium bicarbonate solution and water. The organic phase was dried over sodium sulphate and concentrated. Flash chromatography of the residue on 500 g of silica gel (elution agent methylene chloride/ether 4:1) yielded 2-(2-methoxyethoxy)ethyl bromoacetate as a pale yellow oil.

IR (film): 1740, 1285, 1110 cm$^{-1}$.

(b) A solution of 12.8 g (49 mmol) of triphenylphosphine in 80 ml of toluene was treated within 10 minutes with a solution of 10.7 g (44.3 mmol) of 2-(2-methoxyethoxy)ethyl bromoacetate in 20 ml of toluene. The reaction mixture was stirred at room temperature for 4 hours. The precipitate was filtered off, washed with toluene and dried in a water-jet vacuum. There was obtained [[[2-(2-methoxyethoxy)-ethoxy]carbonyl]methyl]triphenylphosphonium bromide which is processed directly.

(c) A solution of 21 g (41.7 mmol) of [[[2-(2-methoxyethoxy)ethoxy]carbonyl]methyl]triphenylphosphonium bromide in 600 ml of water was treated dropwise with about 50 ml of 1N sodium hydroxide solution up to an alkaline reaction. The reaction mixture was extracted with 500 ml of methylene chloride. The organic phase was dried over sodium sulphate and concentrated. There was obtained [[[2-(2-methoxy-ethoxy)ethoxy]carbonyl]methylene]triphenylphosphorane.

MS: 422 (M+), 301 (base peak) m/e.

(d) A solution of 14.3 g (50 mmol) of 5,5-dibromobarbituric acid in 300 ml of ether was treated with 17.6 g (0.1 mol) of 4-(3-methoxyphenyl)-3-buten-2-one and the mixture was stirred at room temperature for 20 hours. The separated barbituric acid was filtered off. The filtrate was washed in succession with saturated sodium bicarbonate solution and with water. The organic phase was dried over sodium sulphate and concentrated. Flash chromatography of the residue on 1000 g of silica gel (elution agent methylene chloride/ethyl acetate 9:1) yielded (E)-1-bromo-4-(3-methoxyphenyl)-3-buten-2-one as a yellow oil.

MS: 256, 254 (M+), 161 (base peak) m/e.
IR (film): 1697, 1611, 1577, 1263, 990 cm$^{-1}$.

(e) A solution of 14.9 g (35.2 mmol) of [[[2-(2-methoxyethoxy)ethoxy]carbonyl]methylene]triphenylphosphorane (preparation see paragraph (c)) in 100 ml of toluene was treated with 4.48 g (17.6 mmol) of (E)-1-bromo-4-(3-methoxyphenyl)-3-buten-2-one (preparation see paragraph d)). The reaction mixture was stirred at reflux for 2 hours and then filtered. After the addition of 1.63 ml (17.6 mmol) of ethyl bromoacetate, the filtrate was again stirred at reflux for 2 hours. The separated solid was filtered off. The filtrate was concentrated and purified by flash chromatography on 500 g of silica gel (elution agent ether/hexane 10:1). Crystallization of the purified product from methylene chloride/ether/hexane yielded 2-(2-methoxyethoxy)ethyl (E,E)-6-(3-methoxyphenyl)-4-oxo-2,5-hexadienoate of melting point 59°–60°.

MS: 334 (M+), 215, 187 (base peak) m/e.

EXAMPLE 23

(a) 23.1 ml of n-butyllithium solution (1.6M in hexane) were added at −78° to a solution of 5.3 ml (37.0 mmol) of 3,3-diethoxy-1-propyne in 100 ml of absolute tetrahydrofuran, and the mixture was stirred at −78° for a further 30 minutes. Thereafter, a solution of 5.0 g (30.83 mmol) of 4-methoxycinnamaldehyde in 25 ml of tetrahydrofuran was slowly added dropwise. The reaction mixture was stirred at −78° for 2 hours and subsequently treated at −40° with 50 ml of saturated ammonium chloride solution, 50 g of ice and 150 ml of ether. The aqueous phase was extracted twice with ether. The combined organic fractions were dried over magnesium sulphate, filtered and evaporated. The oily residue was chromatographed on 300 g of silica gel with ether/petroleum ether (1:1). There was thereby obtained (E)-6,6-diethoxy-1-(p-methoxyphenyl)-1-hexen-4-yn-3-ol as a light yellowish oil which solidified slowly upon leaving to stand for a long time.

IR (film): 3414(m), 2976(m), 2892(w), 2240(w), 1652(w), 1607(s), 1512(s), 1328(m), 1252(s), 1142(s), 1051(s), 825(m).

(b) A solution of 3.0 g (10.33 mmol) of (E)-6,6-diethoxy-1-(p-methoxyphenyl)-1-hexen-4-yn-3-ol in 15 ml of methylene chloride was added at 0° to a suspension of 27 g of manganese dioxide in 45 ml of methylene chloride. The reaction mixture was subsequently stirred at room temperature for a further 1 hour, filtered over magnesium sulphate and evaporated. The residue was chromatographed on 100 g of silica gel with petroleum ether/ether (2:1), whereupon (E)-6,6-diethoxy-1-(p-methoxyphenyl)-1-hexen-4-yn-3-one was obtained as a light yellowish oil.

IR (film): 2977(m), 2934(w), 2220(w), 1630(s), 1599(s), 1512(s), 1423(m), 1246(s), 1174(s), 1055(s), 830(m).

EXAMPLE 24

A solution of 1.0 g (3.47 mmol) of (E)-6,6-diethoxy-1-(p-methoxyphenyl)-1-hexen-4-yn-3-one in 4 ml of dioxane and 2 ml of 2.2N aqueous hydrobromic acid was stirred at 30° for 18 hours and subsequently treated with 20 ml of ether and 10 ml of water. The aqueous phase was extracted twice with ethyl acetate. The combined organic fractions were dried over magnesium sulphate, filtered and evaporated. The residue was chromatographed on 80 g of silica gel with acetonitrile/water (1:1). The fractions containing the product were extracted with ethyl acetate. The combined ethyl acetate extracts were dried over magnesium sulphate, filtered and evaporated. The residue was recrystallized from ethyl acetate/hexane, whereby there was obtained (E,E)-6-(p-methoxyphenyl)-4-oxo-2,5-hexadienoic acid of melting point 138°–139°.

EXAMPLE A

Crystalline compounds of formulae I and II and pharmaceutically acceptable salts of compounds of formula I are used as active substances for the preparation of hard gelatine capsules, the content of which has the following composition per capsule:

| | |
|---|---|
| Active substance | 50–250.0 mg |
| Lactose powd. | 40.0 mg |
| Lactose cryst. | 230–30.0 mg |
| Maize starch white | 20.0 mg |
| Talc | 8.0 mg |
| Magnesium stearate | 2.0 mg |
| Fill weight per capsule | 250.0 mg |

The active substance and the adjuvants are mixed with one another and the mixture is filled into hard gelatine capsules of suitable size. If desired, the capsules are subsequently provided with a gastric fluid-resistant coating consisting of hydropropylmethylcellulose phthalate.

EXAMPLE B

Non-crystalline compounds of formulae I and II can be used as described hereinafter as active substances for the preparation of soft gelatine capsules. The abbreviations used have the following meanings:
BHA=Butylated hydroxyanisole
BHT=Butylated hydroxytoluene
PEG=Polyethylene glycol (a) 0.2 mg of BHA and 1.0 mg of ascorbyl palmitate are dissolved in 400 mg of PEG 400 at room temperature under a nitrogen atmosphere. The solution is treated with 50–250 mg of active substance at room temperature under nitrogen. After all has dissolved the mixture obtained is filled in liquid form into soft gelatine capsules.

(b) 300 mg of PEG 400 and 100 mg of PEG 4000 are warmed under nitrogen until the mixture has liquefied. Thereafter, 0.1 mg of BHA, 0.1 mg of BHT and 1.0 mg of ascorbyl palmitate are added thereto under nitrogen. After all has dissolved 50–250 mg of active substance are added under nitrogen and dissolved while mixing thoroughly. The liquid is then filled into soft gelatine capsules.

(c) 0.2 mg of BHA, 0.2 mg of BHT and 1.0 mg of ascorbyl palmitate are dissolved in 400 mg of Polysorbate-80 at room temperature under nitrogen. The mixture is treated with 50–250 mg of active substance under nitrogen. After all has dissolved the liquid is filled into soft gelatine capsules.

(d) A mixture of in each case 200 mg of Polysorbate-60 and Polysorbate-80 is warmed. The liquid mixture obtained is treated under nitrogen with 0.2 mg of BHA, 1.0 mg of α-tocopherol and 2.0 mg of ascorbyl palmitate. After all has dissolved 50–250 mg of active substance are added under nitrogen. After mixing thoroughly until solution is complete the mixture obtained is filled into soft gelatine capsules.

We claims:
1. A compound of the formula

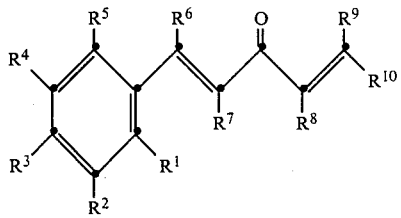

wherein $R^1$, $R^2$, $R^3$, $R^4$ and $R^5$ are independently hydrogen, halogen, lower alkyl, lower alkoxy-lower alkyl, hydroxy, lower alkoxy, lower alkenyloxy, lower alkynyloxy, lower alkoxy-lower alkoxy, acyloxy, aryl-lower alkoxy, lower alkylthio, lower alkoxy-lower alkylthio, lower alkenylthio, lower alkynylthio, aryl-lower alkylthio, optionally substituted amino or trifluoromethyl or two of these substituents which are adjacent jointly and together with the carbon atoms to which they are attached form a 5- to 7-membered ring, provided that of the substituents $R^1$ to $R^5$ at least two are hydrogen and at least one is different from hydrogen; $R^6$ and $R^7$ are hydrogen or lower alkyl; $R^8$ and $R^9$ are hydrogen or lower alkyl or together represent an additional carbon-carbon bond; $R^{10}$ is a group of the formula

—COOR$^{11}$,  —CONR$^{12}$R$^{13}$,  —C(R$^{14}$)=O, (a) (b) (c)

—C(R$^{15}$)(OR$^{16}$)$_2$,  —C(OR$^{17}$)$_3$ or (d) (e)

—C(R$^{18}$)(R$^{19}$)OR$^{20}$;

(f)

$R^{11}$ is hydrogen, lower alkyl, lower alkenyl, lower alkoxy-lower alkyl, lower alkoxy-lower-alkoxy-lower alkyl, aryl or aryl-lower alkyl; $R^{12}$ and $R^{13}$ are hydrogen or lower alkyl or jointly and together with the nitrogen atom represent a 5- to 7-membered saturated heterocyclic group; $R^{14}$ is lower alkyl, or aryl-lower alkyl; $R^{15}$ is hydrogen, lower alkyl, aryl or aryl-lower alkyl; $R^{16}$ is lower alkyl or lower alkoxy-lower alkyl; $R^{17}$ is lower alkyl; $R^{18}$ and $R^{19}$ are hydrogen, lower alkyl, aryl or aryl-lower alkyl; and $R^{20}$ is hydrogen, lower alkyl, lower alkoxy-lower alkyl, lower alkenyl, lower alkynyl, acyl or aryl-lower alkyl; wherein the double bond(s) present in the molecule has (have) the E- and/or Z-configuration; or a pharmaceutically acceptable salt of an acidic compound of formula I with a base or of a basic compound of formula I with an acid.

2. A compound in accordance with claim 1, wherein $R^1$ and $R^2$ are hydrogen and $R^3$, $R^4$ and $R^5$ are lower alkoxy.

3. A compound in accordance with claim 1, wherein $R^1$ and $R^5$ are hydrogen and $R^2$, $R^3$ and $R^4$ are lower alkoxy.

4. A compound in accordance with claim 1, wherein $R^1$, $R^2$ and $R^4$ are hydrogen and $R^3$ and $R^5$ are lower alkoxy.

5. A compound in accordance with claim 1, wherein $R^1$, $R^3$ and $R^4$ are hydrogen and $R^2$ and $R^5$ are lower alkoxy.

6. A compound in accordance with claim 1, wherein $R^1$, $R^2$ and $R^5$ are hydrogen and $R^3$ is hydroxy and $R^4$ is lower alkoxy or $R^3$ and $R^4$ together represent lower alkylenedioxy.

7. A compound in accordance with claim 1, wherein $R^1$, $R^2$, $R^4$ and $R^5$ are hydrogen and $R^3$ is halogen, lower alkoxy, lower alkylthio or trifluoromethyl.

8. A compound in accordance with claim 1, wherein $R^1$, $R^2$, $R^3$ and $R^5$ are hydrogen and $R^4$ is lower alkoxy.

9. A compound in accordance with claim 1, wherein $R^1$, $R^2$, $R^4$ and $R^5$ are hydrogen and $R^3$ is fluorine or methoxy.

10. A compound in accordance with claim 1, wherein $R^1$, $R^2$, $R^3$ and $R^5$ are hydrogen and $R^4$ is methoxy.

11. A compound in accordance with claim 1, wherein $R^6$ and $R^7$ are hydrogen.

12. A compound in accordance with claim 1, wherein $R^8$ and $R^9$ are hydrogen or together represent an additional carbon-carbon bond.

13. A compound in accordance with claim 1, wherein $R^{10}$ is a group of formula (a), (d) or (f), $R^{11}$ is hydrogen, lower alkyl or lower alkoxy-lower alkoxy-lower-alkyl, $R^{15}$ is hydrogen, $R^{16}$ is lower alkyl, $R^{18}$ and $R^{19}$ are hydrogen, and $R^{20}$ is hydrogen, lower alkoxy-lower alkyl or lower alkenyl.

14. A compound in accordance with claim 1, wherein $R^{10}$ is a group of formula (a) or (f), $R^{11}$ is hydrogen, methyl or methoxyethoxyethyl, and $R^{20}$ is hydrogen or 1-ethoxyethyl.

15. A compound in accordance with claim 1 which is (E,E)-6-(3-methoxyphenyl)-4-oxo-2,5-hexadienoic acid.

16. A compound in accordance with claim 1 which is (E,E)-6-(4-methoxyphenyl)-4-oxo-2,5-hexadienoic acid.

17. A compound in accordance with claim 1 which is methyl (2Z, 5E)-6-(4-methoxyphenyl)-4-oxo-2,5-hexadienoate.

18. A compound in accordance with claim 1 which is (E)-6-(4-methoxyphenyl)-4-oxo-5-hexen-2-ynoic acid.

19. A compound in accordance with claim 1 which is selected from the group consisting of:
(E,E)-6-(4-fluorophenyl)-4-oxo-2,5-hexadienoic acid;
(2Z,5E)-6-(4-methoxyphenyl)-4-oxo-2,5-hexadienoic acid;
2-(2-methoxyethoxy)ethyl (E,E)-6-(3-methoxyphenyl)-4-oxo-2,5-hexadienoate; and
2-(2-methoxyethoxy)ethyl (E)-6-(4-methoxyphenyl)-4-oxo-5-hexen-2-ynoate.

20. A pharmaceutical composition comprising a compound of the formula

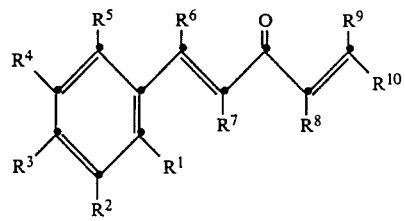

I wherein $R^1$, $R^2$, $R^3$, $R^4$ and $R^5$ are independently hydrogen, halogen, lower alkyl, lower alkoxy-lower alkyl, hydroxy, lower alkoxy, lower alkenyloxy, lower alkynyloxy, lower alkoxy-lower alkoxy, acyloxy, aryl-lower alkoxy, lower alkylthio, lower alkoxy-lower alkylthio, lower alkenylthio, lower alkynylthio, aryl-lower alkylthio, optionally substituted amino or trifluoromethyl or two of these substituents which are adjacent jointly and together with the carbon atoms to which they are attached form a 5- to 7-membered ring, provided that of the substituents $R^1$ to $R^5$ at least two are hydrogen and at least one is different from hydrogen; $R^6$ and $R^7$ are hydrogen or lower alkyl; $R^8$ and $R^9$ are hydrogen or lower alkyl or together represent an additional carbon-carbon bond; $R^{10}$ is a group of the formula

—COOR$^1$,  —CONR$^{12}$R$^{13}$,  —C(R$^{14}$)=O, (a) (b) (c)

-continued

—C(R$^{15}$)(OR$^{16}$)$_2$, —C(OR$^{17}$)$_3$ or
    (d)                    (e)

—C(R$^{18}$)(R$^{19}$)OR$^{20}$;
    (f)

R$^{11}$ is hydrogen, lower alkyl, lower alkenyl, lower alkoxy-lower alkyl, lower alkoxy-lower alkoxy-lower alkyl, aryl or aryl-lower alkyl; R$^{12}$ and R$^{13}$ are hydrogen or lower alkyl or jointly and together with the nitrogen atom represent a 5- to 7-membered saturated heterocyclic group; R$^{14}$ is lower alkyl, or aryl-lower alkyl; R$^{15}$ is hydrogen, lower alkyl, aryl or aryl-lower alkyl; R$^{16}$ is lower alkyl or lower alkoxy-lower alkyl; R$^{17}$ is lower alkyl; R$^{18}$ and R$^{19}$ are hydrogen, lower alkyl, aryl or aryl-lower alkyl; and R$^{20}$ is hydrogen, lower alkyl, lower alkoxy-lower-alkyl, lower alkenyl, lower alkynyl, acyl or aryl-lower alkyl;

wherein the double bond(s) present in the molecule has (have) the E- and/or Z-configuration; or a pharmaceutically acceptable salt of an acidic compound of formula I with a base or of a basic compound of formula I with an acid, and with one or more inert excipients.

21. A composition according to claim 20, in which the compound is (E,E)-6-(3-methoxyphenyl)-4-oxo-2,5-hexadienoic acid.

22. A composition according to claim 20, in which the compound is (E,E)-6-(4-methoxyphenyl)-4-oxo-2,5-hexadienoic acid.

23. A composition according to claim 20, in which the compound is methyl(2Z,5E)-6-(4-methoxyphenyl)-4-oxo-2,5-hexadienoate.

24. A composition according to claim 20, in which the compound is (E)-6-(4-methoxyphenyl)-4-oxo-5-hexien-2-ynoic acid.

25. A composition according to claim 20, in which the compound is selected from the group consisting of:
(E,E)-6-(4-fluorophenyl)-4-oxo-2,5-hexadienoic acid;
(2Z,5E)-6-(4-methoxyphenyl)-4-oxo-2,5-hexadienoic acid;
2-(2-methoxyethoxy)ethyl (E,E)-6-(3-methoxyphenyl)-4-oxo-2,5-hexadienoate; and
2-(2-methoxyethoxy)ethyl (E)-6-(4-methoxyphenyl)-4-oxo-5-hexen-2-ynoate.

26. A method of treating ulcers comprising administering to a subject having this condition a therapeutically effective amount of a compound of the formula

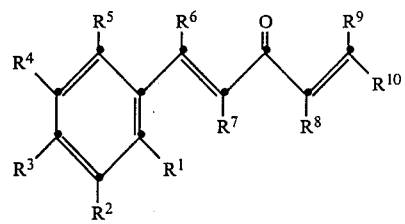

wherein R$^1$, R$^2$, R$^3$, R$^4$ and R$^5$ are independently hydrogen, halogen, lower alkyl, lower alkoxy-lower alkyl, hydroxy, lower alkoxy, lower alkenyloxy, lower alkynyloxy, lower alkoxy-lower alkoxy, acyloxy, aryl-lower alkoxy, lower alkylthio, lower alkoxy-lower alkylthio, lower alkenylthio, lower alkynylthio, aryl-lower alkylthio, optionally substituted amino or trifluoromethyl or two of these substituents which are adjacent jointly and together with the carbon atoms to which they are attached form a 5-to 7-membered ring, provided that of the substituents R$^1$ and R$^5$ at least two are hydrogen and at least one is different from hydrogen; R$^6$ and R$^7$ are hydrogen or lower alkyl; R$^8$ and R$^9$ are hydrogen or lower alkyl or together represent an additional carbon-carbon bond; R$^{10}$ is a group of the formula —COOR$^{11}$, —CONR$^{12}$R$^{13}$, —C(R$^{14}$)=O,
    (a)        (b)           (c)

—C(R$^{15}$)(OR$^{16}$)$_2$, —C(OR$^{17}$)$_3$ or
    (d)                    (e)

—C(R$^{18}$)(R$^{19}$)OR$^{20}$;
    (f)

R$^{11}$ is hydrogen, lower alkyl, lower alkenyl, lower alkoxy-lower alkyl, lower alkoxy-lower alkoxy-lower alkyl, aryl or aryl-lower alkyl; R$^{12}$ and R$^{13}$ are hydrogen or lower alkyl or jointly and together with the nitrogen atom represent a 5- to 7-membered saturated heterocyclic group; R$^{14}$ is lower alkyl, or aryl-lower alkyl; R$^{15}$ is hydrogen, lower alkyl, aryl or aryl-lower alkyl; R$^{16}$ is lower alkyl or lower alkoxy-lower alkyl; R$^{17}$ is lower alkyl; R$^{18}$ and R$^{19}$ are hydrogen, lower alkyl, aryl or aryl-lower alkyl; and R$^{20}$ is hydrogen, lower alkyl, lower alkoxy-lower alkyl, lower alkenyl, lower alkynyl, acyl or aryl-lower alkyl;

whereby the double bond(s) present in the molecule has (have) the E- and/or Z-configuration; or a pharmaceutically acceptable salt of an acidic compound of formula I with a base or of a basic compound of formula I with an acid.

* * * * *